US00PP21275P2

(12) United States Plant Patent
Valenzuela et al.

(10) Patent No.: US PP21,275 P2
(45) Date of Patent: Sep. 7, 2010

(54) ***ALSTROEMERIA* PLANT NAMED 'JAONA'**
(50) Latin Name: *Alstroemeria hybrida*
Varietal Denomination: Jaona

(75) Inventors: Camilo Herrera Valenzuela, Bogotá (CO); Henry Belalcázar Valencia, Bogotá (CO)

(73) Assignee: C.I. Valmar S.A., Bogatá (CO)

( * ) Notice: Subject to any disclaimer, the term of this patent is extended or adjusted under 35 U.S.C. 154(b) by 0 days.

(21) Appl. No.: 12/383,842

(22) Filed: Mar. 27, 2009

(51) Int. Cl.
*A01H 5/00* (2006.01)

(52) U.S. Cl. ..... Plt./309
(58) Field of Classification Search ..... Plt./309
See application file for complete search history.

*Primary Examiner*—June Hwu
(74) *Attorney, Agent, or Firm*—C. A. Whealy

(57) ABSTRACT

A new and distinct cultivar of *Alstroemeria* plant named 'Jaona', characterized by its erect and strong flowering stems; vigorous growth habit; red, white and yellow-colored flowers arranged in rounded symmetrical umbels; and excellent post-production longevity.

2 Drawing Sheets

Botanical designation: *Alstroemeria hybrida.*
Cultivar denomination: 'JAONA'.

BACKGROUND OF THE INVENTION

The present invention relates to a new and distinct cultivar of *Alstroemeria* plant, botanically known as *Alstroemeria hybrida,* commercially used as a cut flower *Alstroemeria,* and hereinafter referred to by the name 'Jaona'.

The new *Alstroemeria* plant is a product of a planned breeding program in Madrid, Cundinamarca, Colombia. The objective of the breeding program was to create new *Alstroemeria* cultivars with attractive flower color and good post-production longevity.

The new *Alstroemeria* plant originated from a cross-pollination conducted by the Inventors in Madrid, Cundinamarca, Colombia in June, 2003 of a proprietary selection of *Alstroemeria hybrida* identified as code number PJA 717, not patented, as the female, or seed, parent with a proprietary selection of *Alstroemeria hybrida* identified as code number PJA 728, not patented, as the male, or seed, parent. The new *Alstroemeria* plant was discovered and selected by the Inventor as a single flowering plant from within the progeny of the stated cross-pollination grown in a controlled greenhouse environment in Madrid, Cundinamarca, Colombia in June, 2004.

Asexual reproduction of the new *Alstroemeria* plant by rhizome divisions in a controlled greenhouse environment in Madrid, Cundinamarca, Colombia since July, 2004, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Jaona'. These characteristics in combination distinguish 'Jaona' as a new and distinct cultivar of *Alstroemeria* plant:

1. Erect and strong flowering stems.
2. Vigorous growth habit.
3. Red, white and yellow-colored flowers arranged in rounded symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the female parent selection have red purple, white and yellow-colored flowers and plants of the male parent selection have red purple and yellow-colored flowers.

Plants of the new *Alstroemeria* can be compared to plants of *Alstroemeria hybrida* 'Koudrey', not patented. In side-by-side comparisons conducted in Madrid, Cundinamarca, Colombia, plants of the new *Alstroemeria* differed primarily from plants of 'Koudrey' in the following characteristics:

1. Plants of the new *Alstroemeria* had longer flowering stems than plants of 'Koudrey'.
2. Plants of the new *Alstroemeria* had larger flowers than plants of 'Koudrey'.
3. Plants of the new *Alstroemeria* and 'Koudrey' differed in flower color.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria.*

The photograph on the first sheet comprises a side perspective view of a typical flowering stem of 'Jaona'.

The photograph on the second sheet is a close-up view of a typical flower of 'Jaona'.

DETAILED BOTANICAL DESCRIPTION

The aforementioned photographs and following observations and measurements describe plants of the new *Alstro-*

*emeria* grown in Madrid, Cundinamarca, Colombia in a polyethylene-covered greenhouse in ground beds. During the production of the plants, day temperatures ranged from 10.5° C. to 31.5° C., night temperatures ranged from 6° C. to 8.5° C. and light levels averaged 21.4 KWH/$m^2$. Plants used for the photographs and description were 44 weeks old. Color references are made to The Royal Horticultural Society Colour Chart, 2007 Edition, except where general terms of ordinary dictionary significance are used.

Botanical classification: *Alstroemeria hybrida* 'Jaona'.

Parentage:

*Female, or seed, parent.*—Proprietary selection of *Alstroemeria hybrida* identified as code number PJA 717, not patented.

*Male, or pollen, parent.*—Proprietary selection of *Alstroemeria hybrida* identified as code number PJA 728, not patented.

Propagation:

*Type.*—By rhizome divisions.

*Time to initiate roots.*—About two weeks at temperatures ranging from 6° C. to 32° C.

*Time to produce a rooted young plant.*—About eight weeks at temperatures ranging from 6° C. to 32° C.

*Root description.*—Fleshy, medium in thickness; close to 155A in color.

*Rooting habit.*—Freely branching; dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright; freely branching, bushy appearance; vigorous growth habit.

*Time from planting to harvest of cut flowers.*—About 126 days.

*Plant height.*—About 110 cm to 120 cm.

*Plant diameter* (*spread*).—About 13.25 cm.

Flowering stem description:

*Aspect.*—Erect.

*Length.*—About 110 cm to 120 cm.

*Diameter.*—About 7 mm.

*Internode length.*—About 5 cm.

*Strength.*—Strong.

*Texture.*—Smooth, glabrous.

*Color.*—Close to 144A.

Foliage description:

*Arrangement.*—Alternate, simple.

*Length.*—About 11.5 cm.

*Width.*—About 4.2 cm.

*Shape.*—Broadly oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper surface: Close to 137C. Developing leaves, lower surface: Close to 138A. Fully expanded leaves, upper surface: Close to N137B; venation, close to 137B. Fully expanded leaves, lower surface: Close to 137B; venation, close to 137B.

*Petioles.*—Length: About 3.2 cm. Diameter: About 7 mm. Texture, upper and lower surfaces: Smooth, glabrous. Color, upper and lower surfaces: Close to 144A.

Flower description:

*Flower type and arrangement.*—Single cup-shaped flowers arranged in compound umbels; flowers face upright to outwardly; perianth segments separate.

*Flowering habit.*—Freely flowering with about ten open flowers and flower buds per inflorescence.

*Natural flowering season.*—Flowering continuous year round in a greenhouse in Colombia; plants begin flowering about 126 days after planting.

*Fragrance.*—Not detected.

*Flower longevity as a cut flower.*—About 10 to 14 days; flowers not persistent.

*Flower buds* (*showing color*).—Length: About 4.4 cm. Diameter: About 1.6 cm. Shape: Obelliptic to obovate. Color: Close to 186A to 186B.

*Umbel height.*—About 10 cm.

*Umbel diameter.*—About 12 cm by 14.5 cm.

*Flower diameter.*—About 6.3 cm.

*Flower length* (*height*).—About 6 cm.

*Flower depth.*—About 6.4 cm.

*Perianth.*—Arrangement: Six arranged in two whorls, each whorl with two lateral and one median segments. Outer perianth, lateral segments: Length: About 6 cm. Width: About 3.6 cm. Shape: Obovate. Apex: Emarginate to nearly cordate. Base: Truncate. Margin: Entire; somewhat sinuate and erose. Texture, upper and lower surfaces: Smooth, glabrous. Color, when opening, upper surface: Close to 60C; towards the base, close to NN155D tinted slightly with close to 65C. Color, when opening, lower surface: Close to 60C; towards the apex, close to 138A; towards the base, close to 186C to 186D. Color, fully opened, upper surface: Close to 63A to 63B; center, close to 59D; towards the base, close to NN155D. Color, fully opened, lower surface: Close to 63C; center, close to 59C; central vein, close to 144A. Outer perianth, median segment: Length: About 5.8 cm. Width: About 3.5 cm. Shape: Obovate. Apex: Emarginate to nearly cordate. Base: Truncate. Margin: Entire; somewhat sinuate and erose. Texture, upper and lower surfaces: Smooth, glabrous. Color, when opening, upper surface: Close to 60B to 60C; towards the base, close to NN155D tinted slightly with close to 65C. Color, when opening, lower surface: Close to 60C; towards the apex, close to 138A; towards the base, close to 186C to 186D. Color, fully opened, upper surface: Close to 60C to 60D; center, close to 59B. Color, fully opened, lower surface: Close to 63A; center, close to 60B; towards the base, close to NN155D. Inner perianth, lateral segments: Length: About 6.2 cm. Width: About 2.2 cm. Shape: Oblanceolate. Apex: Acuminate. Base: Truncate. Margin: Entire; slightly sinuate. Texture, upper and lower surfaces: Smooth, glabrous. Color, when opening, upper surface: Towards the apex, close to 60C; mid-section, close to 4B to 4C; towards the base, close to 65C; random flecks, close to 187B. Color, when opening, lower surface: Towards the apex, close to 185B; mid-section, close to 4C to 4D; towards the base, close to 186D. Color, fully opened, upper surface: Towards the apex, close to 60C to 60D; mid-section, close to 4C; towards the base, close to N155C; random flecks, close to 185A. Color, fully opened, lower surface: Towards the apex, close to 60C to 60D; mid-section, close to 4D; towards the base, close to NN155D. Inner perianth, median segment: Length: About 4.5 cm. Width: About 2.2 cm. Shape: Oblanceolate. Apex: Acuminate. Base: Truncate. Margin: Entire; slightly sinuate. Texture, upper and lower surfaces: Smooth, glabrous. Color, when opening, upper surface: Towards the apex, close to 60B; mid-section, close to 4D; towards the base, close to 157D; random flecks, close to 60B. Color, when opening, lower surface: Towards the apex, close to 185B; mid-section, close to 155B; towards the base, close to NN155C. Color, fully opened, upper surface: Towards the apex and center close to 59D; towards the base, close to NN155D; random flecks, close to 185A. Color, fully opened, lower surface: Towards the apex, close to 70C; center, close to 53C; towards the base, close to NN155D.

*Peduncles.*—Length: About 8 cm. Diameter: About 6 mm. Strength: Strong. Angle: Erect. Texture: Smooth, glabrous. Color: Close to 144A.

*Pedicels.*—Length: About 5.7 cm. Diameter: About 3 mm. Strength: Strong. Angle: About 15° to 30° from the peduncle axis. Texture: Smooth, glabrous. Color: Close to 144A.

*Reproductive organs.*—Stamens: Quantity per flower: Six. Anther shape: Elliptical. Anther length: About 9 mm. Anther diameter: About 3 mm. Anther color: Close to 199B. Pollen amount: Moderate. Pollen color: Close to N199A. Pistils: Quantity per flower: One. Pistil length: About 4.7 cm. Style length: About 3.6 cm. Style color: Close to 186B to 186C. Stigma shape: Three-parted. Stigma color: Close to 60C. Ovary color: Close to 144A to 144B.

*Fruit/seed.*—Fruit and seed development has not been observed.

Disease/pest restistance: Plants of the new *Alstroemeria* have not been observed to be resistant to pathogens and pests common to *Alstroemeria*.

Temperature tolerance: Plants of the new *Alstroemeria* have been observed to tolerate temperatures from about 6° C. to about 32° C.

It is claimed:

1. A new and distinct *Alstroemeria* plant named 'Jaona' as illustrated and described.

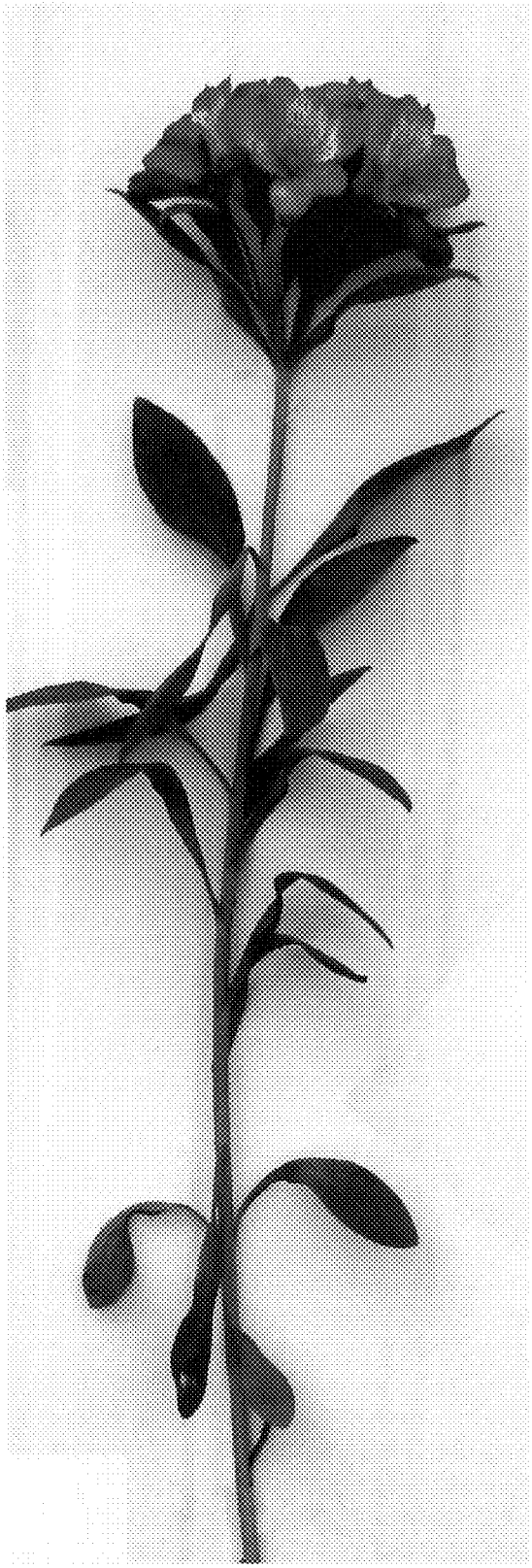

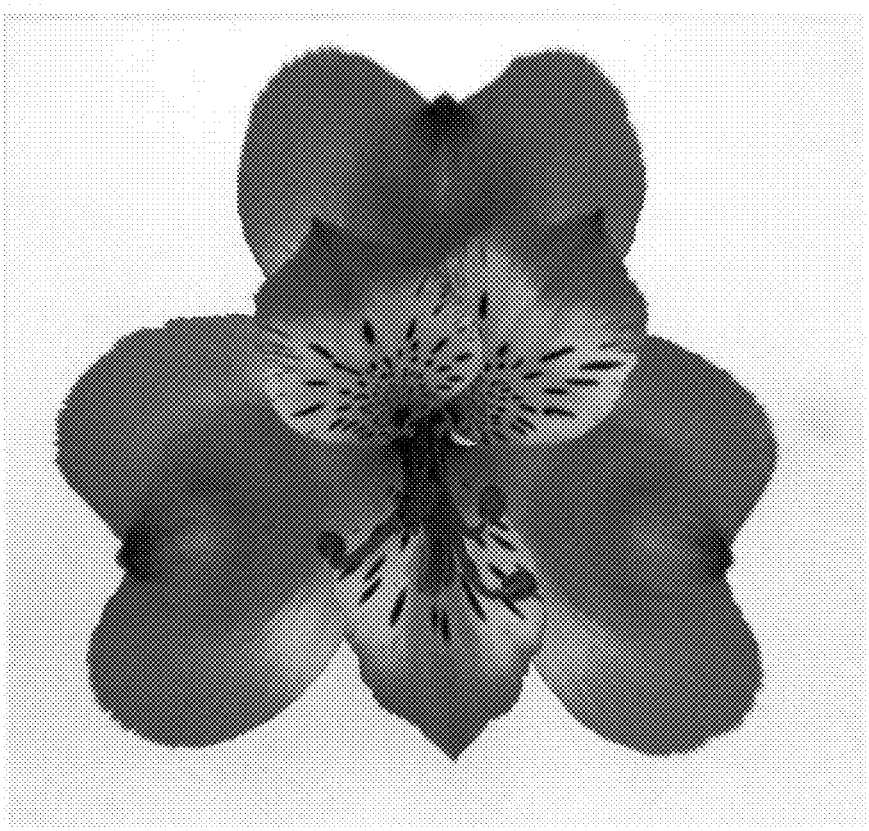

* * * * *